(12) United States Patent
Lee et al.

(10) Patent No.: US 12,686,624 B2
(45) Date of Patent: Jul. 21, 2026

(54) WATER SOFTENING SYSTEM

(71) Applicant: KYUNGDONG NAVIEN CO., LTD., Gyeonggi-do (KR)

(72) Inventors: Soo Young Lee, Seoul (KR); Ji Hyung Yoon, Seoul (KR); So Min Lee, Seoul (KR)

(73) Assignee: KYUNGDONG NAVIEN CO., LTD., Gyeonggi-do (KR)

( * ) Notice: Subject to any disclaimer, the term of this patent is extended or adjusted under 35 U.S.C. 154(b) by 769 days.

(21) Appl. No.: 17/503,357

(22) Filed: Oct. 17, 2021

(65) Prior Publication Data

US 2022/0119284 A1 Apr. 21, 2022

(30) Foreign Application Priority Data

Oct. 16, 2020 (KR) ........................ 10-2020-0134564
Sep. 6, 2021 (KR) ........................ 10-2021-0118397

(51) Int. Cl.
*C02F 1/469* (2023.01)
*A61L 2/18* (2026.01)
(Continued)

(52) U.S. Cl.
CPC .............. *C02F 1/4691* (2013.01); *A61L 2/18* (2013.01); *A61L 2/26* (2013.01); *C02F 1/008* (2013.01);
(Continued)

(58) Field of Classification Search
None
See application file for complete search history.

(56) References Cited

U.S. PATENT DOCUMENTS

2010/0102009 A1* 4/2010 Silva ..................... C02F 1/4691
210/243
2013/0105321 A1* 5/2013 Averbeck ............... B01D 43/00
700/266
(Continued)

FOREIGN PATENT DOCUMENTS

KR 1020170049230 5/2017
KR 1020190134290 12/2019

OTHER PUBLICATIONS

Korean Patent Office, Office Action for related Application No. 10-2021-0118397 issued on Jan. 11, 2023, Korea, 5 bages.

*Primary Examiner* — Louis J Rufo
(74) *Attorney, Agent, or Firm* — McDonald Hopkins LLC

(57) ABSTRACT

Disclosed is a water softening system for removing an ionic material contained in source water supplied from a water source and providing soft water to a source of demand, including a filter unit that removes the least a portion of the ionic material contained in the source water based on an electric force and discharge the soft water, a supply passage that supplies the source water to the filter unit, a discharge passage that discharges water from the filter unit, a circulation passage connecting the discharge passage and the supply passage, a filter management material provider that provides a filter management material used to manage a performance of the filter unit to water that flows along the circulation passage, and a pump that pumps, together with the filter management material, the water that flows along the circulation passage to the filter unit.

15 Claims, 7 Drawing Sheets

(51) Int. Cl.

| | |
|---|---|
| *A61L 2/26* | (2006.01) |
| *C02F 1/00* | (2023.01) |
| *C02F 1/46* | (2023.01) |
| *C02F 1/461* | (2023.01) |
| *C02F 5/00* | (2023.01) |
| *C02F 101/10* | (2006.01) |

(52) U.S. Cl.

CPC ............ *C02F 1/4602* (2013.01); *C02F 1/461*
(2013.01); *C02F 5/00* (2013.01); *A61L*
*2202/11* (2013.01); *C02F 2101/10* (2013.01);
*C02F 2201/005* (2013.01); *C02F 2209/40*
(2013.01); *C02F 2301/046* (2013.01); *C02F*
*2303/16* (2013.01); *C02F 2303/20* (2013.01)

(56) References Cited

U.S. PATENT DOCUMENTS

| | | | | |
|---|---|---|---|---|
| 2016/0280568 A1* | 9/2016 | Wilson | .................. | C02F 1/4691 |
| 2016/0355418 A1* | 12/2016 | Lee | ....................... | C02F 1/4674 |
| 2018/0037477 A1* | 2/2018 | Sasabe | .................... | B01J 47/12 |

* cited by examiner

WATER SOFTENING SYSTEM

CROSS-REFERENCE TO RELATED APPLICATION

This application claims the benefits of priorities to Korean Patent Application No. 10-2020-0134564, filed in the Korean Intellectual Property Office on Oct. 16, 2020 and Korean Patent Application No. 10-2021-0118397, filed in the Korean Intellectual Property Office on Sep. 6, 2021, the entire contents of which are incorporated herein by reference.

TECHNICAL FIELD

The present disclosure relates to a water softening system.

BACKGROUND

A water softening system is a system that produces soft water from source water and supplies the produced soft water to a consumer site. For example, in a water softening system of a points of entry (PoE) type, the consumer site may be a house, and the soft water delivered to a consumer site is in turn delivered to a water faucet, a shower head, and the like that require water.

A filter unit that softens source water by removing an ionic material from the source water is not permanently used, and even when the filter unit is semi-permanently used, it may be smoothly used only when a recycling operation of discharging the collected ionic material is performed periodically.

When a recycling operation is performed, the ionic material may be immediately discharged from the filter unit, but the ionic material may form scales in the filter unit. When scales are formed, an interior of the filter unit may be contaminated. When the scales cover the interior of the filter unit, an area of the interior of the filer unit, in which ions may be adsorbed, may be reduced and may deteriorate a performance of the filter unit. The scales include particulate materials, and may not be smoothly discharged while the recycling operation is performed.

Accordingly, to maintain the performance of the filter unit, a separate descaling process of removing scales formed in the filter unit as well as the recycling operation is necessary. In general, for the descaling process, a scheme of filling citric acid in the filter unit for descaling and discharging the citric acid is used. However, when an amount of scales is excessively large or the scales are firmly stuck to the filter unit, it may not be easy to remove scales only by simply applying the citric acid. Furthermore, when the scales are formed in a death angle area of the filter unit, it is difficult for the citric acid to approach the scales, and thus the scales cannot be easily removed.

Furthermore, biofilms may be formed by germs in the filter unit. The biofilms may contaminate the filter unit similar to the scales, but may not be easily removed by the citric acid. Biofilms may be prevented from being formed by removing the germs in the filter unit through a sterilization process.

SUMMARY

The present disclosure has been made to solve the above-mentioned problems occurring in the prior art while advantages achieved by the prior art are maintained intact.

An aspect of the present disclosure provides a water softening system having an improved scale removal efficiency.

Another aspect of the present disclosure provides a water softening system that may remove biofilms.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, a water softening system for removing at least a portion of an ionic material contained in source water supplied from a water source and providing soft water, in which a smaller amount of the ionic material is contained than in the source water, to a source of demand includes a filter unit that removes the least a portion of the ionic material contained in the source water based on an electric force and discharge the soft water, a supply passage that supplies the source water to the filter unit, a discharge passage that discharges water from the filter unit, a circulation passage connecting the discharge passage and the supply passage, a filter management material provider that provides a filter management material used to manage a performance of the filter unit to water that flows along the circulation passage, and a pump that pumps, together with the filter management material, the water that flows along the circulation passage to the filter unit.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
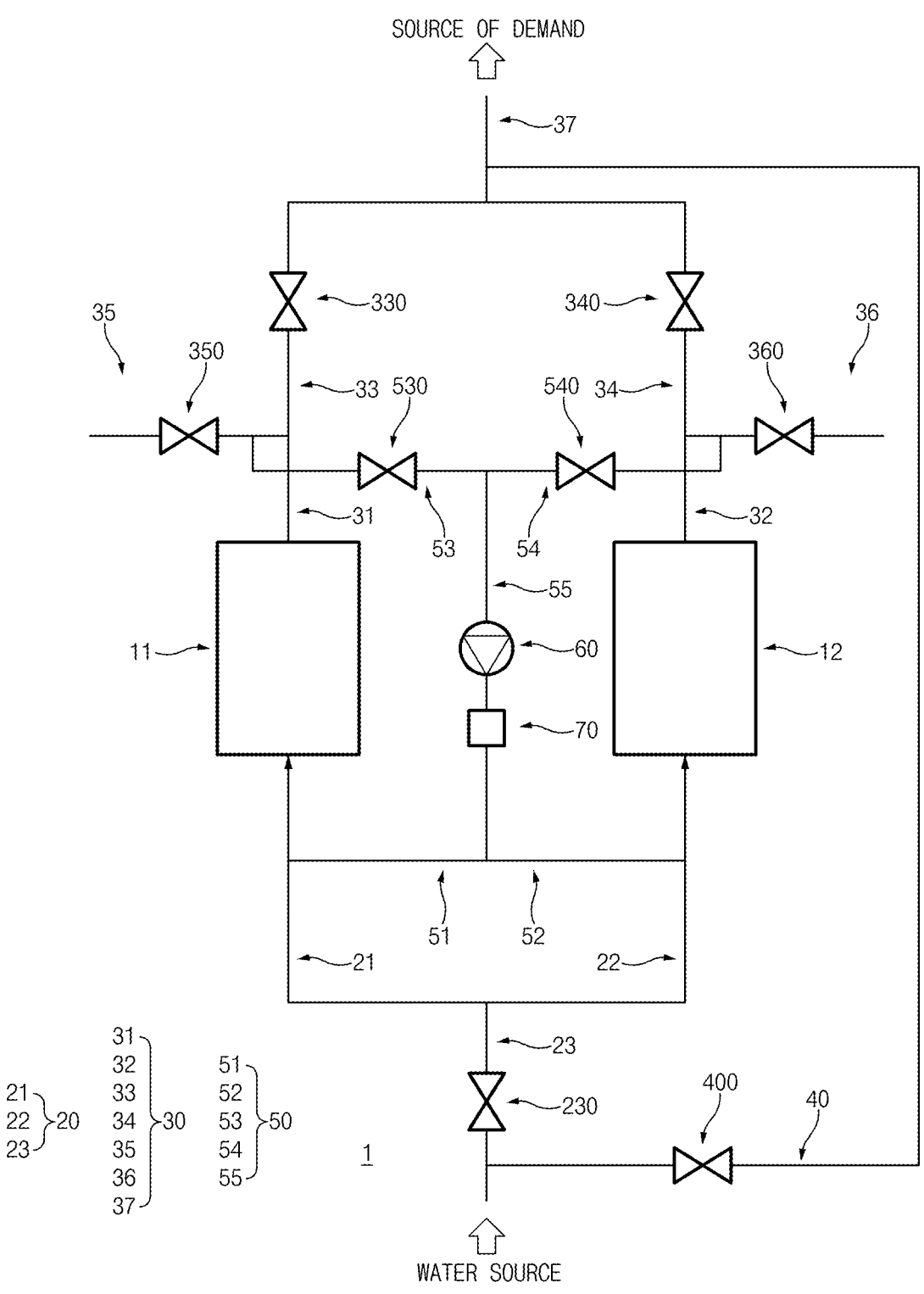
FIG. 1 is a conceptual view of a water softening system according to an embodiment of the present disclosure.

Hereinafter, some embodiments of the present disclosure will be described in detail with reference to the exemplary drawings. Throughout the specification, it is noted that the same or like reference numerals denote the same or like components even though they are provided in different drawings. Further, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present disclosure. The terms are provided only to distinguish the components from other components, and the essences, sequences, orders, and the like of the components are not limited by the terms. When it is described that one element is connected, coupled, or electrically connected to another element, the element may be directly connected or coupled to the other element, but a third element may be connected, coupled, or electrically connected between the elements.

FIG. 1 is a conceptual view of a water softening system 1 according to an embodiment of the present disclosure. Referring to the drawing, a water softening system 1 according to an embodiment of the present disclosure includes filter units 11 and 12 a supply passage 20, a discharge passage 30, a circulation passage 50, a filter management material provider 70, and a pump 60. The water softening system 1 according to the embodiment of the present disclosure may further include a supply valve 230, discharge valves 330 and 340, drainage valves 350 and 360, circulation valves 530 and 540, a bypass passage 400 and a processor (not illustrated). While including the constituent elements, the water softening system 1 may remove at least a portion of an ionic material contained in source water supplied from a water source and provide soft water, in which a smaller amount of the ionic material is contained than in the source water, to a source of demand. The water softening system 1 may selectively perform a soft water mode for discharging soft water from the filter units 11 and 12, and a filter management mode for managing the filter units 11 and 12. Managing the filter units 11 and 12 refers to performing at least one of descaling or sterilizing the filter units 11 and 12.

Supply Passage 20

The supply passage 20 is a passage that is configured to supply source water to the filter units 11 and 12. The supply passage 20 may supply source water from the water source to the filter units 11 and 12. The supply passage 20 may have a tubular shape having an empty interior such that the source water provided from the water source is delivered to the filter units 11 and 12

The supply passage 20 may include a water source passage 23, in which the source water received from the water source flows, and water introduction passages 21 and 22 connecting the water source passage 23 and the filter units 11 and 12. A illustrated, a plurality of water introduction passages 21 and 22 may be arranged in parallel. That is, the source water delivered from the water source passage 23 may be branched through the plurality of water introduction passages 21 and 22 and may be delivered to the filter units 11 and 12. In the embodiment of the present disclosure, although a total of two water introduction passages 21 and 22 such that a first water introduction passage 21 and a second water introduction passage 22 are disposed in parallel, a configuration of the supply passage 20 is not limited thereto, and a plurality of water introduction passages 21 and 22 may be connected to the water source.

The water introduction passages 21 and 22 connect the water source and the filter units 11 and 12. A first water introduction passage 21 may be connected to a first filter unit 11 and a second water introduction passage 22 may be connected to a second filter unit 12. Here, the meanings of "being connected" includes a case of "being directly connected" and a case of "being indirectly connected through another element".

A supply valve 230 may be formed in the supply passage 20 to determine opening/closing of the passage. When the supply valve 230 is disposed in the water source passage 23, only one supply valve 230 is sufficient. However, when the plurality of water introduction passages 21 and 22 are disposed, supply valves 230, the number of which corresponds to the number of the water introduction passages 21 and 22 will be necessary. In the embodiment of the present disclosure, it is described that the supply valve 230 is disposed in the water source passage 23.

The circulation passage 50 is connected to the supply passage 20. In the embodiment of the present disclosure, a first upstream side circulation passage 51 and a second upstream side circulation passage 52 included in the circulation passage 50 may be connected to the first water introduction passage 21 and the second water introduction passage 22.

Discharge Passage 30

The discharge passage 30 is a passage that is configured to discharge water from the filter units 11 and 12. In a removal mode of collecting the ionic material in the source water by the filter units 11 and 12, soft water is discharged through the discharge passage 30, but in a recycling mode, reclaimed water having a larger amount of the ionic material than an amount of the ionic material contained in the source water is discharged, and in a filter management mode, water containing at least one of the removed scales and the residuals obtained as a result of the sterilization is discharged.

The discharge passage 30 include water exit passages 31 32, 33, and 34 for delivering the water from the filter units 11 and 12 to the source of demand, and drainage passages 35 and 36 connected to the water exit passages 31, 32, 33, and 324 to drain the water discharged from the filter units 11 and 12. With respect to locations, at which the drainage passages 35 and 36 are connected to the water exit passages 31, 32, 33, and 34, the water exit passages 31, 32, 33, and 34 may be divided into upstream side water exit passages 31 and 32 and downstream side water exit passages 33 and 34.

Because the plurality of filter units 11 and 12 are provided, the number of discharge passages 30 also may correspond to the number of the filter units 11 and 12, or the discharge passages 30 may be branched, and may be connected to the filter units 11 and 12. The water exit passages 31, 32, 33, and 34 may include a plurality of upstream side water exit passages 31 and connected to the plurality of filter units 11 and 12, respectively, and a plurality of downstream side water exit passages 33 and 34 that are continuous therefrom, respectively. The discharge passage 30 may include a source-of-demand passage 37, in which the plurality of downstream side water exit passages 33 and 34 gather. The plurality of drainage passages 35 and 36 also may be provided, and may be connected to the water exit passages 31, 32, 33, and 34.

In the embodiment of the present disclosure, the first water exit passages 31 and 33 may be connected to the first filter unit 11, and the second water exit passages 32 and 34 may be connected to the second filter units 12. That is, a first upstream side water exit passage 31 may be connected to the first filter unit 11 and a second upstream side water exit passage 32 may be connected to the second filter unit 12.

The first downstream side water exit passage 33 and the first drainage passage 35 may be connected to the first upstream side water exit passage 31, and the second downstream side water exit passage 34 and the second drainage passage 36 may be connected to the second upstream side water exit passage 32. The first downstream side water exit passage 33 and the second downstream side water exit passage 34 may be connected to and merge with the source-of-demand passage 37. However, a configuration of the discharge passage 30 is not limited thereto.

The discharge valves 330 and 340 are constituent elements disposed in the discharge passages 30, respectively, to adjust opening/closing of the discharge passages 30, and may open or close the discharge passages 30 as opening degrees thereof are adjusted. When the discharge passages 30 are closed by the discharge valves 330 and 340, the water is not delivered to a source of demand through the closed discharge passages 30. When the discharge passages 30 are opened by the discharge valves 330 and 340, the water may be delivered to the source of demand through the opened water exit passages 31, 32, 33, and 34, which will be described below, or may be discharged or recovered through the drainage passages 35 and 36, which will be described below. The discharge passages 30 may have shapes of a hollow tubular body such that the water provided from the filter units 11 and 12 flows.

The discharge valves 330 and 340 may be disposed in the discharge passages 30 to determine opening/closing of the discharge passages 30. When the discharge valves 330 and 340 are disposed in the source-of-demand passage 37, only one discharge valve is sufficient. However, when the discharge valves 330 and 340 are disposed in the plurality of water exit passages 31, 32, 33, and 34, the number of the discharge valves 330 and 340 needs to correspond to the number of the water exit passages 31, 32, 33, and 34. In the embodiment of the present disclosure, it is described that the discharge valves 330 and 340 are disposed in the water exit passages 31, 32, 33, and 34 That is, the first discharge valves 330 may be disposed in the first water exit passages 31 and 34, and the second discharge valves 340 may be disposed in the second water exit passages 32 and 34.

The discharge valves 330 and 340 may be disposed in the downstream side water exit passages 33 and 34, respectively. That is, in the embodiment of the present disclosure, the first discharge valve 330 may be disposed in the first downstream side water exit passage 33, and the second discharge valve 340 may be disposed in the second downstream side water exit passage 34. Accordingly, the discharge valves 330 and 340 may not interrupt the water from being delivered from the upstream side water exit passages 31 and 32 to the drainage passages 35 and 36.

At least one of the discharge valves 330 and 340 may be controlled by the processor to be maintained in an opened state during an operation of the water softening system 1. Then, the discharge valves 330 and 340 that are maintained in the opened state may be the discharge valves 330 and 340 disposed in the discharge passages 30 connected to the filter units 11 and 12 that perform a removal mode. Accordingly, even while any one of the filter units 11 and 12 perform a recycling mode, the soft water discharged from the filter units 11 and 12 that perform the removal mode may be delivered to the source of demand. Accordingly, the plurality of filter units 11 and 12 are provided as in the embodiment of the present disclosure, the filter units 11 and 12 alternately perform the recycling mode and the removal mode, and the discharge valves 330 and 340 are controlled in correspondence to the modes, and thus the soft water may be provided with no stop.

The circulation passage 50 is connected to the discharge passage 30. In the embodiment of the present disclosure, a first downstream side circulation passage 53 and a second downstream side circulation passage 54 included in the circulation passage 50 may be connected to the first drainage passage 35 and the second drainage passage 36. However, the circulation passage 50 may be connected to the water exit passages 31, 32, 33, and 34.

The drainage passages 35 and 36 are constituent elements that are connected to the water exit passages 31, 32, 33, and 34 to drain the water in the water in the water exit passages 31, 32, 33, and 34.

The water that has passed through the filter units 11 and 12 may be discharged through the drainage passages 35 and 36. In particular, when the filter units 11 and 12 are operated in the recycling mode, the reclaimed water discharged through the water exit passages 31, 32, 33, and 34 may be drained to the outside through the drainage passages 35 and 36 to be discarded.

However, the water is not always discharged, and whether the water is to be discharged and an amount of the discharged water may be adjusted. Accordingly, the drainage valves 350 and 360 may be provided in the drainage passages 35 and 36 for opening and closing the drainage passages 35 and 36. In the embodiment of the present disclosure, because the drainage passages 35 and 36 include the first drainage passage 35 and the second drainage passage 36, the first drainage valve 350 may be disposed in the first drainage passage 35 and the second drainage valve 360 may be disposed in the second drainage passage 36.

When the circulation passage 50 is connected to the drainage passages 35 and 36, the circulation passage 50 may be connected to one site of the drainage passages 35 and 36 located on an upstream side of the drainage valves 350 and 360 with respect to a direction, in which the water flows along the drainage valves 350 and 360. Accordingly, the flows of the water in the circulation passage 50 may be restricted by the drainage valves 350 and 360.

Circulation Passage 50

The circulation passage is a passage that forms a closed circuit including the supply passage 20, the filter units 11 and 12, the discharge passages 30, and the circulation passage 50 by connecting the discharge passages 30 and the supply passage 20. Accordingly, the water may circulate along the above-described circuit of the circulation circuit 50, and when the water carries the filter management material, the filter units 11 and 12 may be descaled or sterilized while the water circulates.

The circulation passage 50 may include upstream side circulation passages 51 and 52, downstream side circulation passages 53 and 54, a common circulation passage 55 connecting the upstream side circulation passages 51 and 52 and the downstream side circulation passages 53 and 54. The upstream side circulation passages 51 and 52 may be connected to the common passage 20, and the downstream side circulation passages 53 and 54 may be connected to the discharge passage 30. The upstream side circulation passages 51 and 52 may be connected to one site of the supply passage 20 that is located on a downstream side of the supply valve 230 with respect to a direction, in which the water flows in the supply passage 20. The downstream side circulation passages 53 and 54 may be connected to one site of the discharge passage 30 that is located on an upstream side of the discharge valves 330 and 340 with respect to a direction, in which the water flows in the discharge passage 30. Accordingly, in a situation, in which the supply valve 230 and the discharge valves 330 and 340 are closed, water may circulate along the circulation passage 50.

The circulation valves 530 and 540 may be disposed to open and close the circulation passage 50. In detail, the first circulation valve 530 and the second circulation valve 540 may be disposed in the first downstream side circulation passage 53 and the second downstream side circulation passage 54, respectively. However, disposition locations of the circulation valves 530 and 540 are not limited thereto.

Pump 60

The pump 60 may be disposed in the circulation passage 50 to pump the water in the circulation passage 50. Because the filter management material may flow in the circulation passage 50 together with the water, the pump 60 may pump the filter management material to the filer units 11 and 12 together with the water. In the embodiment of the present disclosure, the pump 60 may pump the water in the supply passage 20 to the discharge passage 30 through the circulation passage 50 together with the filter management material.

Filter Management Material Provider 70

The filter management material provider 70 may be provided in the circulation passage 50 to provide the filter management material used to manage performances of the filter units 11 and 12 to the water that flows along the circulation passage 50. Being used to manage the performances of the filter units 11 and 12 means that the performances of the filter units 11 and 12 are maintained or the performances of the filter units 11 and 12, the performances of which deteriorated, are improved by removing scales formed in the filter units 11 and 12 or sterilizing the germs in the filter units 11 and 12 to prevent formation of biofilms. In the embodiment of the present disclosure, it is described that the filter management material provider 70 and the pump 60 are disposed in the common circulation passage 5. However, the filter management material provider 70 and the pump 60 may be disposed at another portion of the circulation passage 50, and a plurality of filter management material providers 70 and a plurality of pumps 60 may be disposed inn the drainage passages 35 and 36 and the water introduction passages 21 and 22.

The filter management material provider 70 may include at least one of citric acid and a sterilization material as the filter management material. Accordingly, the filter management material provider 70 may include a citric acid storage tank for storing citric acid as the filter management material and discharging the citric acid. The citric acid stored in the citric acid storage tank may be provided to the filter units 11 and 12 to be used to remove scales as the water in the circulation tank 50 flows.

The filter management material provider 70 may include an electrolysis/sterilization module. The electrolysis/sterilization module may generate the sterilization material as the filter management material by applying electricity to the water and discharge the generated sterilization material. The electrolysis/sterilization module may include a sterilization material generator configured to generate the sterilization material by using electricity, and a sterilization material storage tank for storing the generated sterilization material.

The sterilization material generator may be controlled by the processor, and may be operated for a least a portion of a period of time, for which the pump 60 is not operated, to generate the sterilization material that is to be stored in the sterilization material storage tank and store the generated sterilization material in the sterilization material storage tank. The stored sterilization material may be provided to the filter units 11 and 12 as the water flows in the circulation passage 50, and may be used to prevent generation of biofilms through sterilization.

Filter Units 11 and 12

The filter units 11 and 12 are constituent elements that generate the soft water by removing ionic material in the source water. The filter units 11 and 12 are provided in the supply passages 20, respectively, and may discharge the soft water including less ion material than the source water by removing at least a portion of the ionic material included in the supplied source water by an electrical force. The operation mode may be referred to as the removal mode. The filter units 11 and 12 may discharge the reclaimed water including more ionic material than that source water by discharging the ionic material collected in the removal mode together with the supplied source water. The operational state may be referred to as the recycling mode. The filter units 11 and 12 may selectively perform any one of the removal mode and the recycling mode. Although it has been described that the plurality of filter units 11 and 12 are provided and the two filter units 11 and 12 including the first and second filter units 11 and 12 are disposed, the configurations thereof are not limited thereto.

The filter units 11 and 12 may remove the ionic material in an electrical deionization scheme. In more detail, the scheme of removing the ionic material includes the electrical deionization scheme. When a DC voltage is applied to charged particles in an electrolyte, positive charged particles travel to a negative electrode and negative charged particles travel to a positive electrode. This is called electrophoresis. The electrical deionization scheme refers to a scheme of removing ionic materials in water by adsorbing or moving the ionic material through electrodes or an ion exchange membrane based on a principle of an electrical force (electrophoresis).

The electrical deionization scheme includes schemes, such as electrodialysis (ED), Electro deionization (EDI), continuous electro deionization (CEDI), and capacitive deionization (CDI) The filter units 11 and 12 in an ED scheme includes electrodes and an ion exchange membrane. Furthermore, the filter units 11 and 12 in an EDI scheme includes electrodes, an ion exchange membrane, and an ion exchange resin. In contrast, the filter units 11 and 12 in the CDI scheme include neither an ion exchange membrane nor an ion exchange resin, or does not include an ion exchange resin.

The filter units 11 and 12 according to the embodiment of the present disclosure may remove the ionic material in, among the electrical deionization schemes, the capacitive deionization (CDI) scheme. The CDI scheme refers to a scheme of removing ions by using a principle of adsorbing and desorbing ions (or ionic material) to and from a surface of an electrode with an electrical force.

Figure 2:
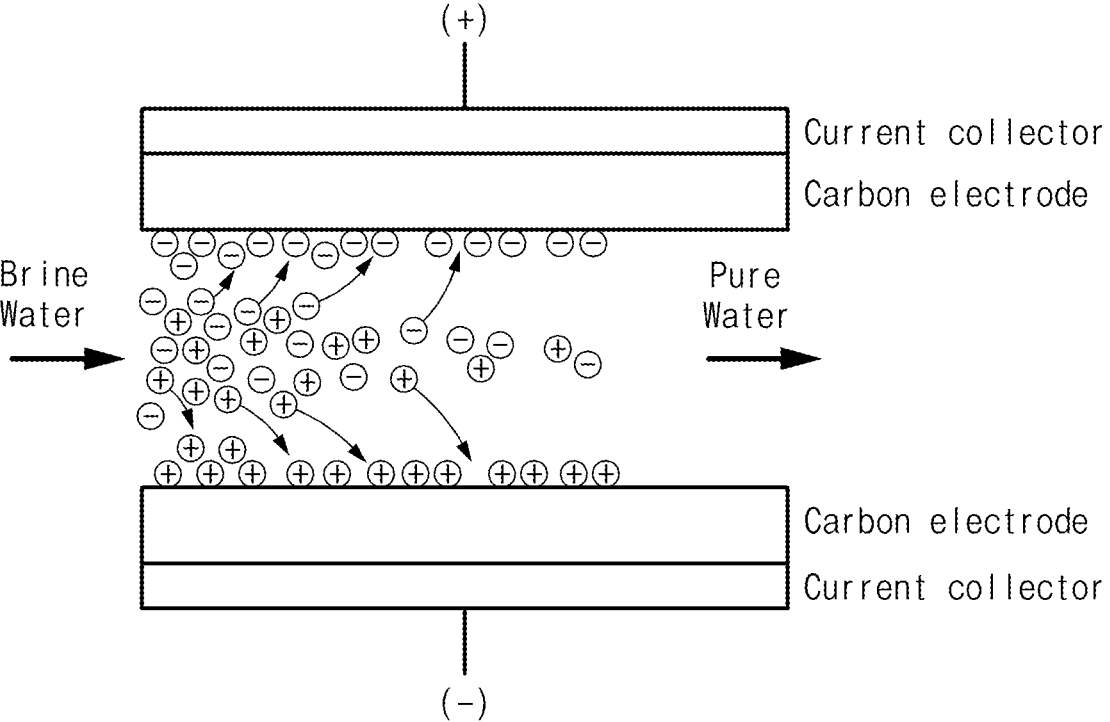
FIG. 2 is a conceptual view illustrating a principle of removing an ionic material in a CDI scheme.
Figure 3:
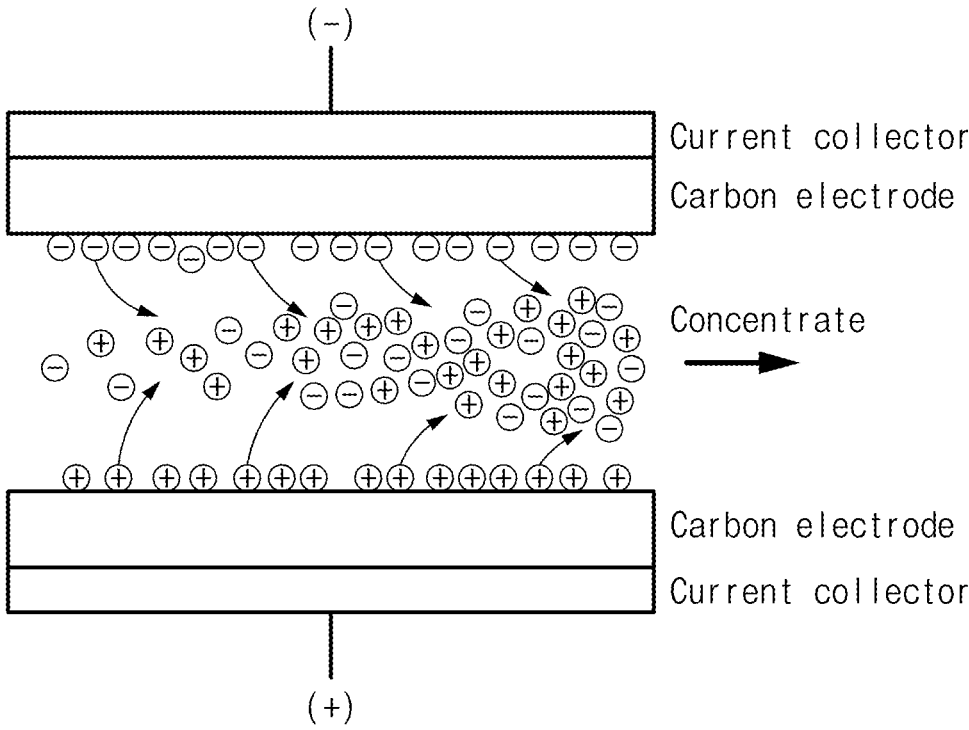
FIG. 3 is a conceptual view illustrating a principle of recycling an electrode in a CDI scheme.

FIG. 2 is a conceptual view illustrating a principle of removing an ionic material in a CDI scheme. FIG. 3 is a conceptual view illustrating a principle of recycling an electrode in a CDI scheme.

Referring further to FIGS. 2 and 3, the removal mode and the recycling mode in the CDI scheme will be described. As illustrated in FIG. 2, in a state, in which a voltage is applied to electrodes, water containing ions passes between the electrodes, negative ions travel to a positive electrode and positive ions travel to a negative electrode. That is, adsorption occurs. Due to the adsorption, ions in the water may be removed. In this way, a method of, by the filter units 11 and 12, removing an ionic material in the water that passes through the filter units 11 and 12 is called the removal mode.

However, adsorption capacities of the electrodes are limited. Accordingly, adsorption continues, the electrodes reach a state, in which ions cannot be adsorbed any more. To prevent this, it is necessary to desorb the ions adsorbed to the electrode to recycle the electrodes. To achieve this, as illustrated in FIG. 3, a voltage that is opposite to a voltage applied to the electrodes in the removal mode may be applied or a voltage may not be applied. In this way, a mode of recycling the electrodes by the filter units 11 and 12 is called the recycling mode. The recycling mode may be performed before or after the removal mode.

Accordingly, for the operation, the filter units 11 and 12 may include electrodes. The filter units 11 and 12 may selectively perform any one of the removal mode of removing the ionic material in the electrical deionization scheme through the electrode, and the recycling mode of recycling the electrodes. Accordingly, when the source water is supplied to the filter units 11 and 12, the soft water may be generated by removing a portion of the ionic material in the source water and may be discharged by the filter units 11 and 12 in the removable mode, and the ionic material of the electrodes is provided to the source water and the water, of which the content of the ionic material has been increased, may be discharged by the filter units 11 and 12 in the recycling mode.

The filter units 11 and 12, as descried above, may be connected to the supply passages 20 and the drainage passages 35 and 36 to receive the water through the supply passages 20 and discharge the treated water through the drainage passages 35 and 36. The source water delivered from the water source may be provided to the filter units 11 and 12, and the filter units 11 and 12 may generate the source water by removing the ionic material from the provided source water and discharge the generated source water, or generate the reclaimed water by sending out the ionic material and discharge the generated reclaimed water.

Bypass Passage 40

The bypass passage 40 is a passage for supplying the source water to the user when the soft water that has passed through the filter units 11 and 12 to the source of demand in the filter management mode. The bypass passage 40 may connect one site of the supply passage 20 located on an upstream side of the supply valve 230 with respect to a direction, in which the water flows, and one site of the discharge passage 30 located on a downstream side of the discharge valves 330 and 340 with respect to a direction, in which the water flows. Accordingly, when the supply valve 230 and the discharge valves 330 and 340 are submerged and the water cannot flow through the filter units 11 and 12, the water may be guided to the bypass passage 40.

A bypass valve 400 may be disposed in the bypass passage 40 to open and close the bypass passage 40. Because the water does not need to flow through the bypass passage 40 in a situation, in which the soft water may be supplied to the source of demand in the soft water mode, the bypass valve 400 may be closed. However, in the filter management mode, the soft water cannot be supplied to the source of demand and it is necessary to supply the source water through the bypass passage 40, and thus the bypass valve 400 may be opened.

Processor

The processor is a constituent element including an element that may perform logical operations for performing a control command, and may include a central processing unit (CPU). The processor may be connected to the elements to transmit signals according to the control commands to the element, and may be connected to the sensors and the acquirers to receive the acquired information in a form of signals. Accordingly, in the embodiment of the present disclosure, the processor may be electrically connected to the valves, the filter units 11 and 12, the pump 60, and the filter management material provider 70 included in the water softening system 1. Because the processor may be electrically connected to the elements, it may be connected to the elements by wire or may further include a communication module that may perform communication wirelessly for mutual communications.

The water softening system 1 may further include a storage medium, and control commands performed by the processor may be stored in the storage medium to be utilized. The storage medium may be a device such as a hard disk drive (HDD), a solid state drive (SSD), a server, a volatile medium, or a nonvolatile medium, but the kinds thereof are not limited thereto. In addition, the storage medium may further store data that is necessary to allow the processor to perform an operation.

Figure 4:
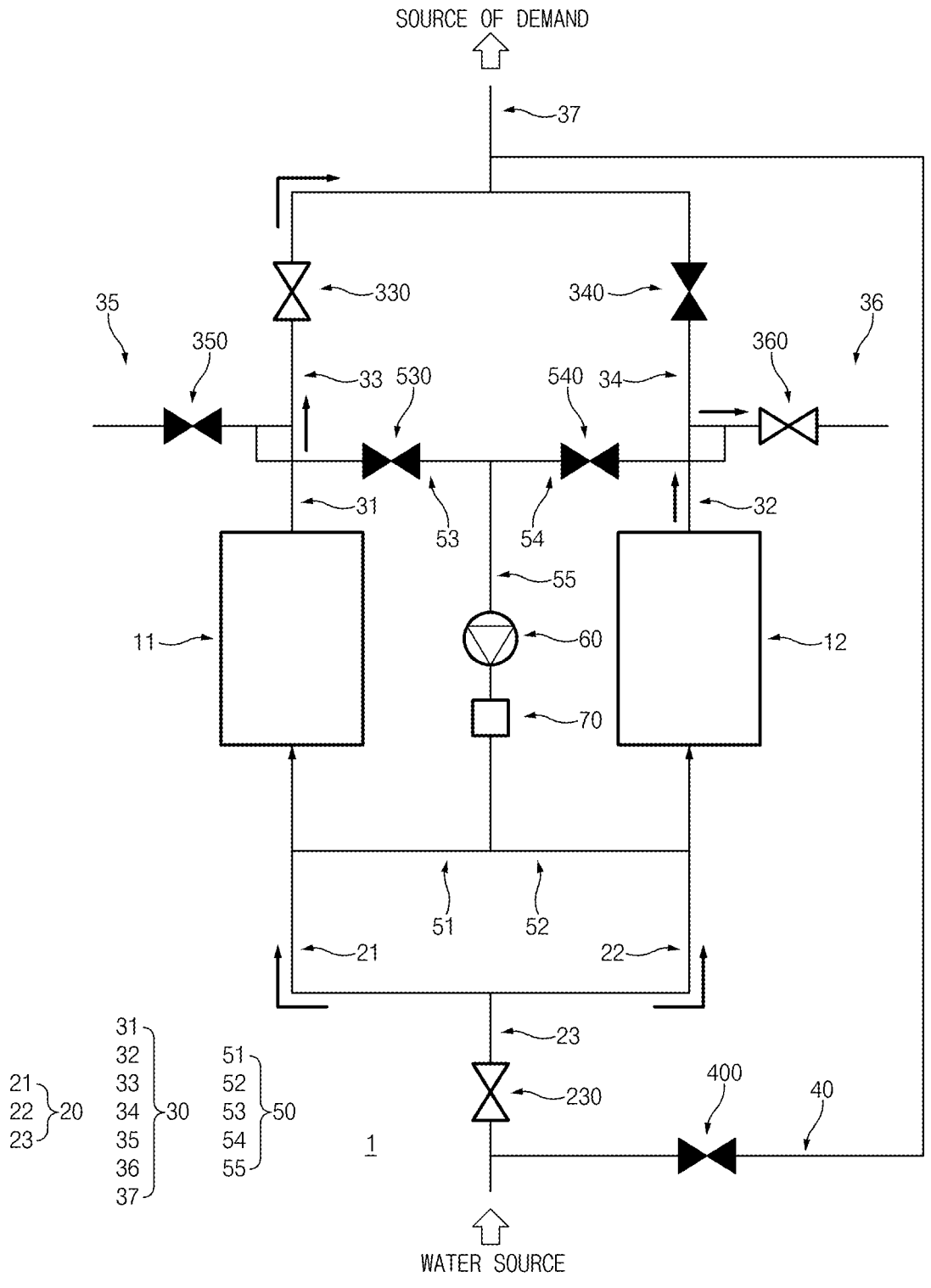
FIG. 4 is a conceptual view illustrating a situation, in which a water softening system is operated in a soft water mode, according to an embodiment of the present disclosure.

A scheme of controlling the water softening system 1 by the processor will be described with reference to FIGS. 4, 5, and 7. FIG. 4 is a conceptual view illustrating a situation, in which a water softening system 1 is operated in a soft water mode, according to an embodiment of the present disclosure.

Referring to the drawings, the water softening system 1 according to the embodiment of the present disclosure may be operated in the soft water mode. In the soft water mode, the processor may control the filter units 11 and 12 to be operated, control the pump 60 not to be operated, control the supply valve 230 and the discharge valves 330 and 340 to be opened, and control the bypass valve 400 to be closed. Furthermore, the processor may control the circulation valves 530 and 540 to be closed. Accordingly, the water does not flow through the bypass passage 40 and the circulation passage 50 but may be recycled while passing through the filter units 11 and 12 or softened by the filter units 11 and 12 to be provided to the source of demand.

FIG. 4 illustrates a situation, in which the first filter unit 11 is operated in the removal mode and the second filter unit 12 is operated in the recycling mode. Accordingly, the first discharge valve 330 may be opened and the first drainage valve 350 may be closed such that the source water that has passed through the first filter unit 11 is softened to be provided to the source of demand. Accordingly, the second discharge valve 340 may be closed and the second drainage valve 360 may be opened such that the source water that has passed through the second filter unit 12 is softened to be provided to the source of demand. When the modes of the first filter unit 11 and the second filter unit 12 are converted to the recycling mode and the removal mode, respectively, after lapse of a specific period of time, the operations of the drainage valves 350 and 360 and the discharge valves 330 and 340 also may be performed in a reverse way.

Figure 5:
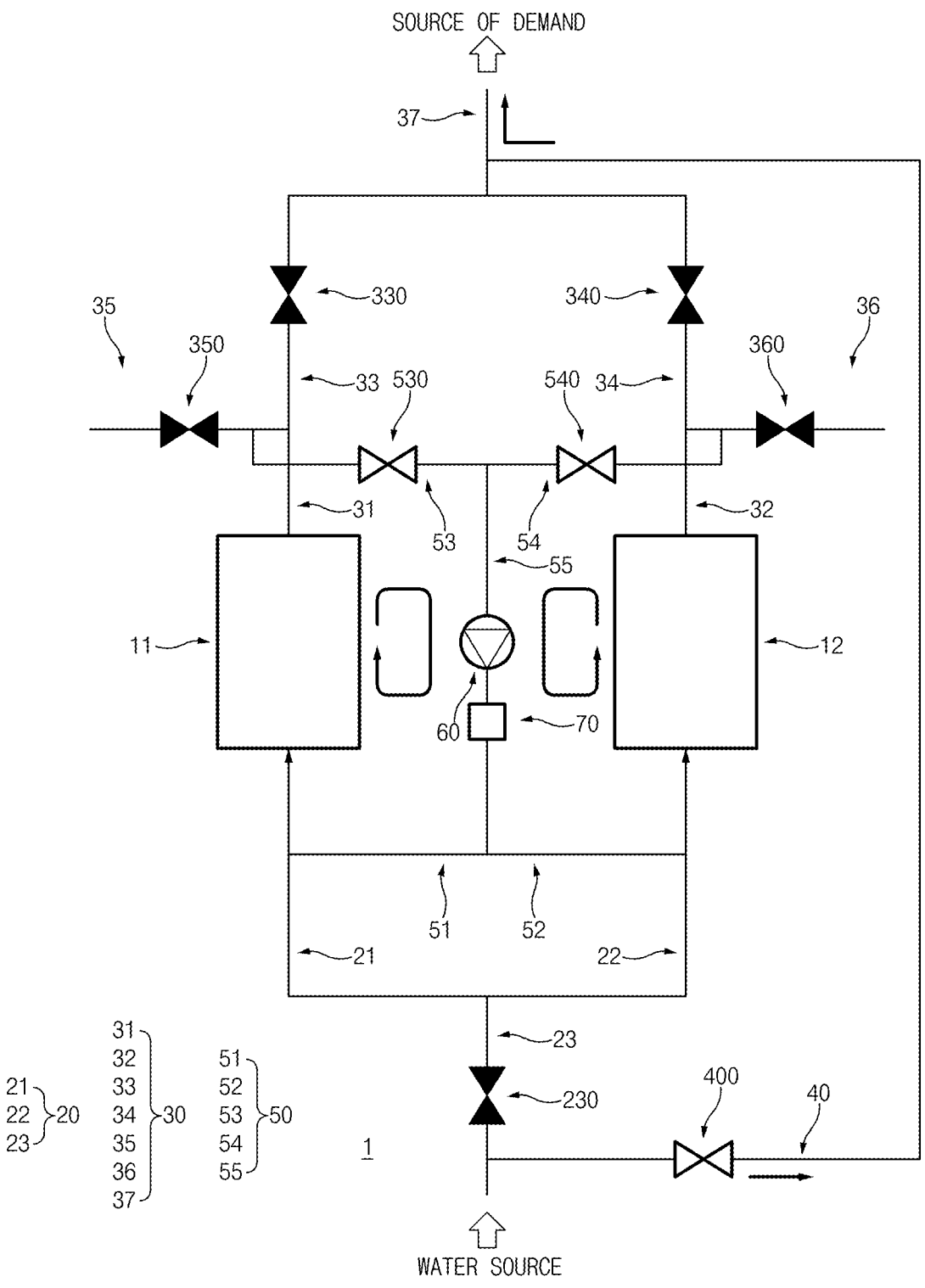
FIG. 5 is a conceptual view illustrating a situation, in which a water softening system is operated in a filter management mode, according to an embodiment of the present disclosure.

FIG. 5 is a conceptual view illustrating a situation, in which a water softening system 1 is operated in a filter management mode, according to an embodiment of the present disclosure.

In the filter management mode, the processor may control the supply valve 230 and the discharge valves 330 and 340 to be closed, the operations of the filter units 11 and 12 to be stopped, and the pump 60 to be operated. Furthermore, the processor may control the circulation valves 530 and 540 and the bypass valve 400 to be opened, and control the drainage valves 350 and 360 to be closed. Accordingly, the water gets stuck between the supply valve 230 and the discharge valves 330 and 340, and the above-described closed circuit is constituted. Due to the pump 60, the flows of the water may be formed along the closed circuit, and the water may circulate. Then, the filter management material provided by the filter management material provider 70 located in the circulation passage 50 may be provided to the water and may circulate together. Accordingly, the filter management material may be provided to the filter units 11 and 12 located in the closed circuit, and may sterilize or descale the filer units 11 and 12. Furthermore, the source water may be provided from the water source to the source of demand along the bypass passage 40.

As in the embodiment of the present disclosure, when the two filter units 11 and 12 are disposed, two closed circuits may be formed. In detail, as indicated by the arrows of the drawings, a closed circuit having a sequence of the first filter unit 11—the first drainage passage 35—the first downstream side circulation passage 53—the common circulation passage 55—the first upstream side circulation passage 51—the first water introduction passage 21, and a closed circuit having a sequence of the second filter unit 12—the second drainage passage 36—the second downstream side circulation passage 54—the common circulation passage 55—the second upstream side circulation passage 52—the second water introduction passage 22 maybe formed.

As the filter management material circulates, the contaminants of the filter units 11 and 12 may be removed better than when the filter management material stays. Because the water may be sterilized or descaled in a clean in place (CIP) scheme of performing sterilization or descaling while not being accompanied by decomposition by the system, the water softening system 1 may be easily maintained and repaired.

In FIG. 5, the pump 60 pumps the water in the discharge passage 30 to the supply passage 20 through the circulation passage 50 together with the filter management material. However, according to a modification of the embodiment of the present disclosure, the pump 60 may be operated in a reverse direction.

Figure 6:
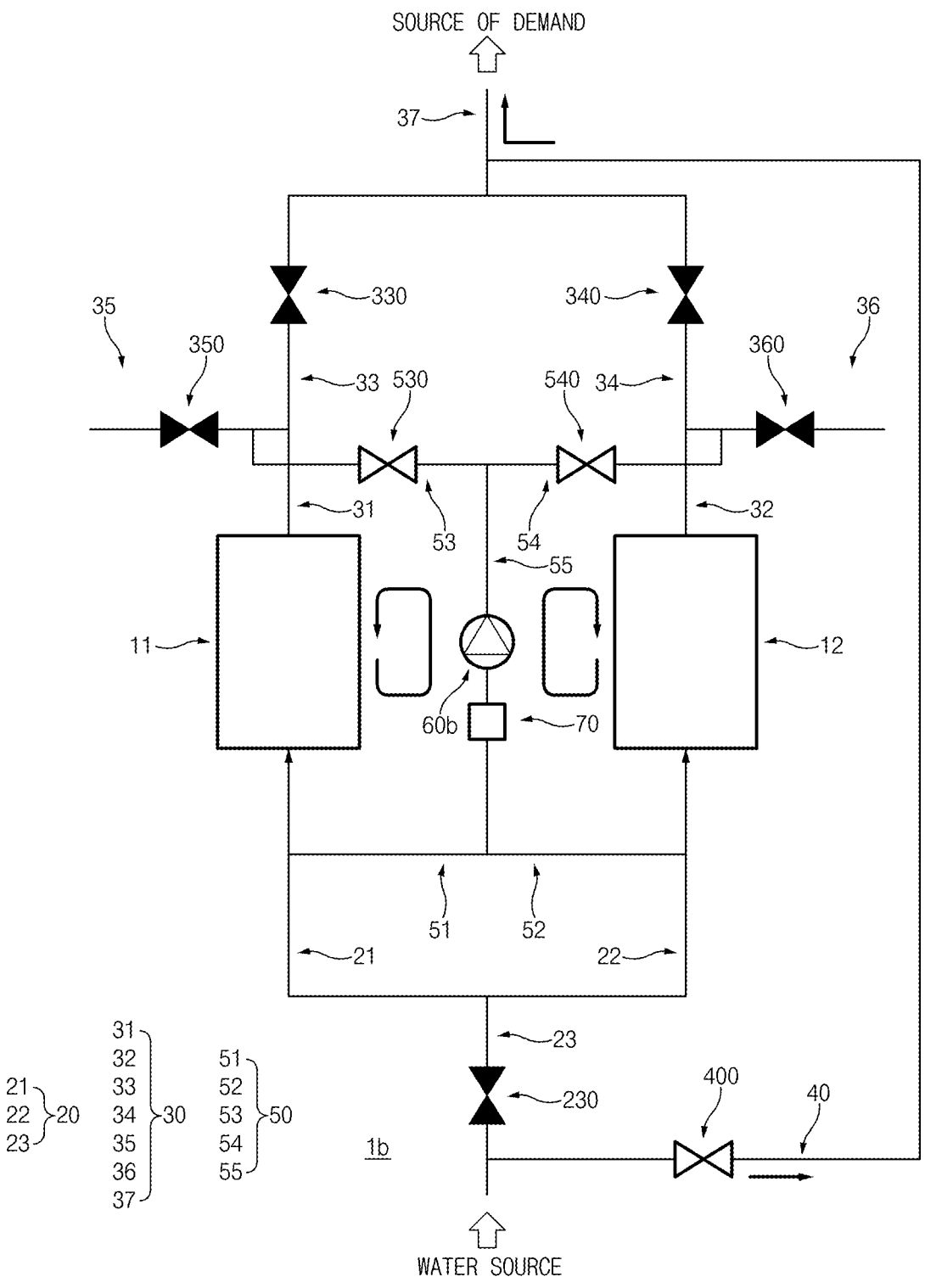
FIG. 6 is a conceptual view illustrating a situation, in which a water softening system is operated in a filter management mode, according to a modification of an embodiment of the present disclosure.

FIG. 6 is a conceptual view illustrating a situation, in which a water softening system 1b is operated in a filter management mode, according to a modification of an embodiment of the present disclosure.

According to a modification of the embodiment of the present disclosure, the pump 60b may pump the water in the supply passage 20 to the discharge passage 30 through the circulation passage 50 together with the filter management material. That is, the water and the filer management material may circulate in a closed circuit in a direction that is opposite to the circulation direction.

When the source water passes through the filter units 11 and 12, a larger amount of the ionic material is located at inlet ends of the filter units 11 and 12 than at outlet ends thereof, and scales may be easily formed. As in FIG. 6, when the filter management material, in particular, the citric acid circulates in an opposite direction to a direction, in which the source water passes the filter units 11 and 12, a large amount of scales formed at the inlet ends of the filter units 11 and 12 are stricken to easily separate the scales from the filter units 11 and 12.

Figure 7:
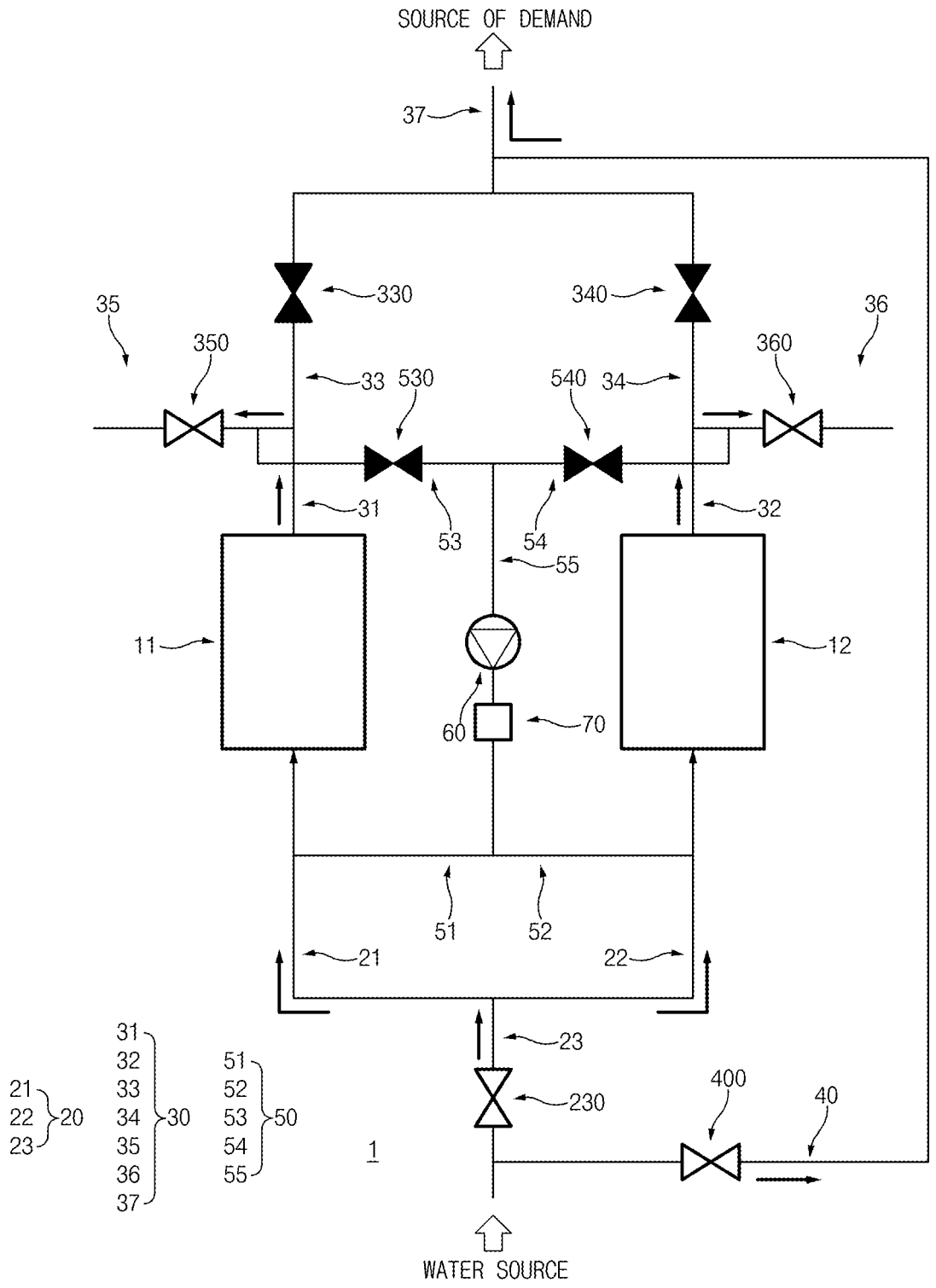
FIG. 7 is a conceptual view illustrating a situation, in which a water softening system drains water after finishing a filter management mode, according to an embodiment of the present disclosure.

FIG. 7 is a conceptual view illustrating a situation, in which a water softening system 1 drains water after finishing a filter management mode, according to an embodiment of the present disclosure.

The processor may control the operation of the pump 60 to be stopped after lapse of a first period of time from a time point, at which the filter management mode is executed and the operation of the pump 60 starts. The processor may open the supply valve 230 and the drainage valves 350 and 360 to drain the water discharged from the filter units 11 and 12. Accordingly, the water containing the filter management material and the contaminants may be discharged through the drainage passages 35 and 36.

However, the processor may open the supply valve 230 and the drainage valves 350 and 360 after lapse of a second period of time after the operation of the pump 60 is stopped. The filter management material stays in the filter units 11 and 12 for the second period of time for further descaling or sterilization.

The first period of time may be 2 minutes or less. A total period of time performed in the filter management mode may be 5 minutes or less.

When the water is completely drained, the processor may perform the above-described control such that the water softening system 1 is operated in the soft water mode again. The processor may control the valves and the pump 60 to perform the filter management mode for a specific cycle.

The processor may control the electrolysis/sterilization module to be operated for at least a portion of a period of time, for which the pump 60 is not operated, to generate a sterilization material that is to be stored in the sterilization material storage tank. The citric acid may be supplemented in the citric acid tank by the user.

Meanwhile, the processor may circulate the water a plurality of times. The processor may allow the filter units 11 and 12 to be sterilized or descaled by causing the water filled in the circulation passage 50 to circulate for the above-described first period of time with the pump 60 after receiving the filter management material from the filter management material provider 70, in the filter management mode. Thereafter, the processor may stop the pump 60 for a third period of time. Thereafter, the processor may control the filter management material provider 70 to further provide the filter management material to the water filled in the circulation passage 50, and may operate the pump 60 again to sterilize or descale the filter units 11 and 12 for a specific period of time at a second time. Thereafter, the processor may drain the water containing the filter management material and the contaminants through the drainage passages 35 and 36 by opening the drainage valves 350 and 360. Because the water circulates a plurality of times, the contaminants deposited in the filter units 11 and 12 may be initially removed while the water circulates initially, and the residual contaminants may be removed during the next circulation.

Meanwhile, in the filter management mode, the processor may repeatedly control the supply valve 230, the drainage valves 350 and 360, and the pump 60 a plurality of times such that the pump 60 is operated and then stopped, and the water is drained. That is, the circulation and the discharge of the water may be performed again after the water circulates, is discharged, and is filled again in the circulation passage 50 through the supply passage 20. Accordingly, a cycle of introduction, circulation, and discharge of the water may be repeated a plurality of times in the filter management mode.

Meanwhile, the processor may control the filter management material provider 70 while causing the water to circulate a plurality of times such that the filter material provided by the filter management material provider 70 at a first time and the filter material provided by the filter management material provider 70 at another time may be different. For example, the citric acid may circulate together with the water for descaling at the first time, at which the water circulates, and the sterilization material may circulate together with the water for sterilization at another time. The circulation sequence of the citric acid and the sterilization material may be a sequence of the citric acid-the sterilization material, and may be a sequence of the sterilization material-the citric acid reversely. Furthermore, the processor may cause the citric acid and the sterilization material to be provided together with the water and cause the water to circulate.

Accordingly, scales may be effectively removed.

The biofilms formed in the water softening system may be effectively removed.

Although it may have been described until now that all the elements constituting the embodiments of the present disclosure are coupled to one or coupled to be operated, the present disclosure is not essentially limited to the embodiments. That is, without departing from the purpose of the present disclosure, all the elements may be selectively coupled into one or more elements to be operated. Furthermore, because the terms, such as "comprising", "including", or "having" may mean that the corresponding element may be included unless there is a specially contradictory description, it should be construed that another element is not extruded but may be further included. In addition, unless defined otherwise, all terms used herein, including technical or scientific terms, have the same meanings as those generally understood by those skilled in the art to which the present disclosure pertains. The terms, such as the terms defined in dictionaries, which are generally used, should be construed to coincide with the context meanings of the related technologies, and are not construed as ideal or excessively formal meanings unless explicitly defined in the present disclosure.

The above description is a simple exemplification of the technical spirits of the present disclosure, and the present disclosure may be variously corrected and modified by those skilled in the art to which the present disclosure pertains without departing from the essential features of the present disclosure. Accordingly, the embodiments disclosed in the present disclosure is not provided to limit the technical spirits of the present disclosure but provided to describe the present disclosure, and the scope of the technical spirits of the present disclosure is not limited by the embodiments. Accordingly, the technical scope of the present disclosure should be construed by the attached claims, and all the technical spirits within the equivalent ranges fall within the scope of the present disclosure.

What is claimed is:

1. A water softening system for removing at least a portion of an ionic material contained in source water supplied from a water source and providing soft water, in which a smaller amount of the ionic material is contained than in the source water, to a source of demand, the water softening system comprising:

filter units including a first filter unit and a second filter unit, each configured to remove at least a portion of the ionic material contained in the source water based on an electric force and to discharge the soft water;

a supply passage including a first water introduction passage connected to the first filter unit for supplying the source water to the first filter unit, and a second water introduction passage connected to the second filter unit for supplying the source water to the second filter unit;

a discharge passage including a first upstream side water exit passage connected to the first filter unit for discharging water from the first filter unit, and a second upstream side water exit passage connected to the second filter unit for discharging water from the second filter unit;

a circulation passage connecting the discharge passage and the supply passage, including a first downstream side circulation passage connected to the first upstream side water exit passage, a second downstream side circulation passage connected to the second upstream side water exit passage, and a common circulation passage connected to the first water introduction passage, the second water introduction passage, the first downstream side circulation passage, and the second downstream side circulation passage;

a filter management material provider disposed in the common circulation passage to provide a filter management material used to manage a performance of the filter units to water that flows along the circulation passage;

a pump disposed in the common circulation passage to pump, together with the filter management material, the water that flows along the circulation passage to the filter units;

a supply valve disposed in the supply passage to open and close the supply passage;

a discharge valve disposed in the discharge passage to open and close the discharge passage;

a first circulation valve disposed in the first downstream side circulation passage;

a second circulation valve disposed in the second downstream side circulation passage; and a processor electrically connected to the filter units, the supply valve, the discharge valve, the first circulation valve, the second circulation valve and the pump;

wherein the circulation passage is connected to one site of the supply passage, which is located on a downstream side of the supply valve with respect to a direction, in which the water flows in the supply passage, and one site of the discharge passage, which is located on an upstream side of the discharge valve with respect to a direction, in which the water flows in the discharge passage, and wherein the processor is configured to, in a filter management mode:

control the supply valve and the discharge valve to be closed;

control the first circulation valve and the second circulation valve to be opened;

control an operation of the filter unit to be stopped; and control the pump to be operated.

2. The water softening system of claim 1, wherein the pump pumps, together with the filter management material, the water in the discharge passage to the supply passage through the circulation passage.

3. The water softening system of claim 1, wherein the pump pumps, together with the filter management material, the water in the supply passage to the discharge passage through the circulation passage.

4. The water softening system of claim 1, further comprising:

a drainage valve, wherein the discharge passage includes:

a water exit passage configured to deliver the water from the filter unit to the source of demand; and a drainage passage connected to the water exit passage to drain the water discharged from the filter unit, wherein the drainage valve is disposed in the drainage passage to open and close the drainage passage, wherein the processor is further electrically connected to the drainage valve, and wherein the processor is configured to:

control the operation of the pump to be stopped after lapse of a first period of time from a time point, at which the pump starts the operation thereof; and open the supply valve and the drainage valve such that the water discharged from the filter unit is drained.

5. The water softening system of claim 4, wherein the processor is configured to:

open the supply valve and the drainage valve such that the water discharged from the filter unit is drained after lapse of a second period of time from a time point, at which the operation of the pump is stopped.

6. The water softening system of claim 4, wherein the processor is configured to:

further control the filer management material provider such that the filter management material is further supplied to the water in the circulation passage after the first period of time elapses and the operation of the pump is stopped;

further control the pump such that the pump stops the operation thereof again after performing the operation thereof for a specific period of time; and open the supply valve and the drainage valve such that the water in the circulation passage is drained.

7. The water softening system of claim 4, wherein the processor is configured to, in the filter management mode:

control the pump, the supply valve, and the drainage valve such that the operation of the pump is stopped after being performed, and the water is drained.

8. The water softening system of claim 7, wherein the processor is configured to, in the filter management mode:

when the controlling of the pump, the supply valve, and the drainage valve such that the operation of the pump is stopped after being performed, and the water is drained is repeated a plurality of times, control the filter management material provider such that a kind of a filter management material provided by the filter management material provider at a first time, and a kind of a filter management material provided by the filter management material provider at another time are different.

9. The water softening system of claim 1, wherein the filter management material provider includes an electrolysis/sterilization module configured to generate a sterilization material for sterilizing the filter unit as the filter management material by applying electricity to the water and discharge the sterilization material.

10. The water softening system of claim 9, further comprising:

a processor electrically connected to the electrolysis/sterilization module, wherein the electrolysis/sterilization module includes:

a sterilization material generator configured to generate the sterilization material; and a sterilization material storage tank configured to store the generated sterilization material, and wherein the processor is configured to:

control the electrolysis/sterilization module to be operated for at least a portion of a period of time, for which the pump is not operated, to generate the sterilization material that is to be stored in the sterilization material storage tank.

11. The water softening system of claim 1, wherein the filter management material provider includes:

a citric acid storage tank configured to store citric acid for removing scales formed in the filter unit as the filter management material and discharge the citric acid.

12. The water softening system of claim 1, wherein the filter management material includes citric acid for removing scales formed in the filter unit, and a sterilization material for sterilizing the filter unit.

13. The water softening system of claim 1, further comprising:

a bypass passage connecting one site located on an upstream side of the supply valve with respect to a direction, in which the water flows in the supply passage and one site located on a downstream side of the discharge valve with respect to a direction, in which the water flows in the discharge passage.

14. The water softening system of claim 1, further comprising:

a bypass valve disposed in the bypass passage to open and close the bypass passage, wherein the processor is further electrically connected to the bypass valve, wherein the processor is configured to:

in a soft water mode, in which the soft water is discharged from the filter unit, control the filter unit to be operated, control the pump not to be operated, control the supply valve and the discharge valve to be opened, and control the bypass valve to be closed; and in the filter management mode, further control the bypass valve to be opened.

15. The water softening system of claim 1, wherein the processor is configured to:

control the supply valve, the discharge valve, and the pump to perform the filter management mode for a specific cycle.

* * * * *